United States Patent [19]

Holtkamp, Sr.

[11] Patent Number: Plant 6,533

[45] Date of Patent: Jan. 17, 1989

[54] AFRICAN VIOLET PLANT NAMED LIBRA

[75] Inventor: Reinhold Holtkamp, Sr., Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 56,413

[22] Filed: Jun. 1, 1987

[51] Int. Cl.[4] ..... A01H 5/00

[52] U.S. Cl. ..... Plt./69

[58] Field of Search ..... Plt. 69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An African violet plant named Libra, characterized by its single solid purple flowers; upright flower stems curving toward the center; profuse flowering; vigorous growth habit; very attractive girl-type leaves, round, slightly serrated with a small light green center; long lasting and non-dropping flowering habit.

1 Drawing Sheet

The present invention comprises a new and distinct cultivar of African violet plant, botanically known as *Saintpaulia ionantha,* and hereinafter referred to by the cultivar name Libra.

The new cultivar was referred to during the breeding and selection process by the designation G17/1, and is a product of a planned breeding program. The new cultivar was originated from a cross made by applicant in a controlled breeding program in Haffen, Federal Republic of Germany. The female, or seed parent was a cultivar designated D150/4 red girl. The male, or pollen parent was a cultivar designated 7/78 Burgundy.

Libra was discovered and selected by me as a flowering plant within the progeny of the stated cross in a controlled environment in Haffen, Federal Republic of Germany. Asexual reproduciton of the new cultivar by leaf cuttings, as performed by me at Haffen, Federal Republic of Germany, has demonstrated that the combination of characteristics as herein disclosed for the new cultivar are firmly fixed and retained through successive generations of asexual reproduciton.

Libra has not been observed under all possible environmental conditions. The phenotpye may vary significantly with variations in environment such as temperature, light intensity and day length. The following observations, measurements and values describe the new cultivar as grown in 10 cm pots in Haffen, Federal Republic of Germany and Nashville, Tenn. under greenhouse conditions which closely approximate those generally used in commercial practice.

The following traits have been repeatedly observed and are determined to be basic characteristics of Libra which in combination distinguish this African violet as a new and distinct cultivar:

1. Strong upright flower stems curving toward the center.
2. Long-lasting, non-dropping, single solid purple flowers.
3. Each plant carries 8 or more upright flower stems, each of which carries 7 to 9 flowers.
4. Profuse flowering.
5. Seed capsule pushes through.
6. Vigorous grower.
7. Plant saleable 9–10 weeks after potting.
8. Very attractive girl-type leaf, round, slightly serrated with a small light green center.

9. After maturity, the flowers dry off and remain on the peduncle without becoming infected by botrytis.

The accompanying color photographic drawing shows a typical specimen plant of the new cultivar. The colors appearing in the photograph are as true as possible with color illustrations of the type.

In the following description, color references are made to The Royal Horticultural Soceity Colour Chart (R.H.S.), except where general colors of ordinary significance are referred to. Color values were taken under natural light conditions at approximately 1:00 p.m. in Nashville, Tenn. Under color growing conditions and more intensive lighting, the purple color becomes more intense.

Botanical classification: *Saintpaulia ionantha,* Ramat., cv. Libra.

Parentage:

*Male parent.*—3/78 Burgundy.

*Female parent.*—D150/4 red girl.

Propagation: The new cultivar holds its distinguishing characteristics through successive propagations by leaf cuttings and by division of shoots.

Plant: From 10 cm to 11 cm tall when grown in pots, and approximately 18–20 cm in diameter when fully grown. The growth rate is vigorous.

*Leaves.*—Shape: Very round, girl-type. Diameter: 55–65 mm. Texture: Velvety, shiny. Ribs and Veins: Upperside visible, underside very well pronounced, light green and shiny; purplish on the very young leaves. Color (upper side): Green 139A. Color (under side): Yellow-green 148D. Petioles: Strong, upright, light green with purplish red touch on side toward flowers, hairy.

*Flowers.*—Buds: Purple, bell-shaped, 8–9 mm just before opening. Sepals: Five (5) in number, purple-green. Calyx: Funnel-shaped. Aspect: Spear-shaped, hairy. Peduncle: Strong, upright, purplish brown, hairy.

*Individual flowers.*—Size: 35 to 40 mm. Shape: Conventional, single violet-shaped; 3 large and 2 small petals. Color (upper side): Red purple 72A-B. Color (under side): Purple violet 80B. Borne: The long flower stems carry 7–9 and more flowers each on strong, upright peduncles that are free standing above the leaves, and that are curving toward the center of the plant. Flower habit:

Flowers 9–10 weeks after potting. Corolla: Compact flower head, free-standing above the leaves.

*Reproductive organs.*—Stamens: Two (2) in number. Anthers: Two, composed of 4 cells. Filaments: 5 mm long, yellowish green, with purple at edges. Pollen Color: Yellow 7A. Styles: 7 mm, purple, hairy base of ovary light green. Roots: Normally developed, white when young, turning slightly brownish when older.

Disease resistance: Good

General observations: Libra has a very attractive appearance through its medium green, round girl-type leaves with a light green center. A tight bouquet of flowers on strong peduncles, free-standing above the leaves, is composed of solid purple single flowers contrasting with the bright yellow anthers. Occasionally, 1 or 2 additional small petals develop over the 2 smaller petals. The flowers are long-lasting and non-dropping.

I claim:

1. A new and distinct cultivar of African violet named Libra, as described and illustrated, and particularly characterized by its single solid purple flowers; upright flower stems curving toward the center; profuse flowering; vigorous growth habit; very attractive girl-type leaves, round, slightly serrated with a small light green center; and long lasting and non-dropping flowering habit.

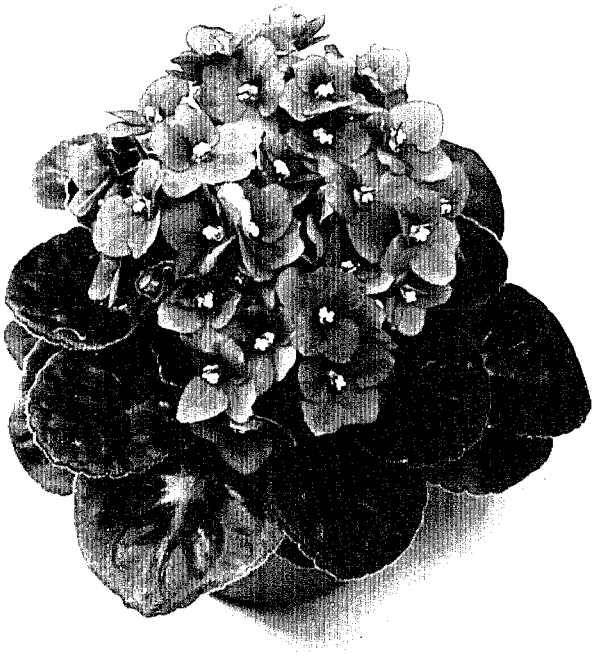

* * * * *